(12) United States Patent
Wang et al.

(10) Patent No.: US 12,097,325 B2
(45) Date of Patent: Sep. 24, 2024

(54) SYSTEMS AND DEVICES FOR PREVENTING OCCLUSION OF A SUCTION LINE RESIDENT IN A MEDICAL DEVICE

(71) Applicant: NEVAP, INC., San Jose, CA (US)

(72) Inventors: Benjamin R. Wang, San Jose, CA (US); Brenton Hanlon, Palo Alto, CA (US)

(73) Assignee: NEVAP, INC., San Jose, CA (US)

( * ) Notice: Subject to any disclaimer, the term of this patent is extended or adjusted under 35 U.S.C. 154(b) by 681 days.

(21) Appl. No.: 16/686,031

(22) Filed: Nov. 15, 2019

(65) Prior Publication Data

US 2020/0155780 A1   May 21, 2020

Related U.S. Application Data

(60) Provisional application No. 62/767,939, filed on Nov. 15, 2018.

(51) Int. Cl.
*A61M 16/04* (2006.01)

(52) U.S. Cl.
CPC .... *A61M 16/0463* (2013.01); *A61M 16/0434* (2013.01); *A61M 16/0465* (2013.01)

(58) Field of Classification Search
CPC .......... A61M 16/0463; A61M 16/0479; A61M 16/0475; A61M 16/0477; A61M 16/0434; A61M 16/04; A61M 16/0402; A61M 16/0431; A61M 16/0436; A61M 16/0443; A61M 16/0445; A61M 16/0447; A61M 16/045; A61M 16/0454; A61M 16/0459; A61M 16/0465; A61M 16/0472; A61M 16/0481; A61M 16/0484; A61M 16/0486; A61M 25/00; A61M 25/04
See application file for complete search history.

(56) References Cited

U.S. PATENT DOCUMENTS 3,583,404 A   6/1971   Mcwhorter
3,995,643 A   12/1976  Merav
(Continued)

FOREIGN PATENT DOCUMENTS

CN   202699807 U   1/2013
CN   203763615 U   8/2014
(Continued)

OTHER PUBLICATIONS

Covidien, TaperGuard Endotracheal and Specialty Tubes, 2014, Date Retrieved Oct. 29, 2 pages.
(Continued)

*Primary Examiner* — Bradley H Philips
*Assistant Examiner* — Savannah L Gabriel
(74) *Attorney, Agent, or Firm* — Resonance IP Law, PC

(57) ABSTRACT

Tube systems may include a tube with an inflatable balloon that is affixed to, and circumferentially surrounding an exterior portion of the tube. The inflatable balloon may be positioned between the first open end and the second open end of the tube. The tube may be flexible and hollow and may have a first open end and a second open end. The tube may include a suction line, a suction line port, and a spacer that extends from an exterior surface of the tube and is positioned proximate to the suction line port. The spacer may be configured to prevent occlusion of the suction line port.

15 Claims, 22 Drawing Sheets

100C

(56) References Cited

U.S. PATENT DOCUMENTS

| | | | |
|---|---|---|---|
| 4,278,081 A | 7/1981 | Jones | |
| 4,327,721 A | 5/1982 | Goldin et al. | |
| 4,437,856 A | 3/1984 | Valli | |
| 4,693,243 A | 9/1987 | Buras | |
| 4,840,173 A | 6/1989 | Porter, III | |
| 4,973,305 A | 11/1990 | Golzer | |
| 5,146,916 A | 9/1992 | Catalani | |
| 5,311,864 A | 5/1994 | Huerta | |
| 5,389,074 A | 2/1995 | Parker et al. | |
| 5,501,215 A | 3/1996 | Huerta | |
| 5,513,627 A | 5/1996 | Flam | |
| 5,715,816 A | 2/1998 | Mainiero et al. | |
| 5,819,723 A | 10/1998 | Joseph | |
| 6,048,332 A | 4/2000 | Duffy | |
| 6,460,540 B1 | 10/2002 | Klepper | |
| 6,837,868 B1* | 1/2005 | Fajnsztajn | A61M 25/04 604/101.03 |
| 7,669,600 B2 | 3/2010 | Morejon | |
| 8,196,584 B2 | 6/2012 | Maguire | |
| 8,357,118 B2 | 1/2013 | Orr | |
| 8,535,265 B2 | 9/2013 | Burnett et al. | |
| 9,327,091 B2 | 5/2016 | Wang et al. | |
| 9,446,213 B2 | 9/2016 | Wang | |
| 9,579,475 B2 | 2/2017 | Wang | |
| 10,071,212 B1 | 9/2018 | Riesberg | |
| 2004/0116898 A1 | 6/2004 | Hawk | |
| 2004/0255951 A1 | 12/2004 | Grey | |
| 2008/0011304 A1 | 1/2008 | Stewart | |
| 2008/0047562 A1* | 2/2008 | Colburn | A61M 16/0479 128/207.14 |
| 2008/0172120 A1 | 7/2008 | Fenn et al. | |
| 2008/0283052 A1* | 11/2008 | Young | A61M 16/0479 128/207.15 |
| 2009/0260632 A1* | 10/2009 | Abnousi | A61M 16/04 128/207.15 |
| 2010/0147309 A1 | 6/2010 | Cuevas et al. | |
| 2010/0269830 A1 | 10/2010 | Layer et al. | |
| 2011/0023884 A1 | 2/2011 | Cuevas et al. | |
| 2011/0139159 A1 | 6/2011 | Nelson | |
| 2011/0190737 A1* | 8/2011 | Rocco | A61M 27/00 604/544 |
| 2012/0000471 A1 | 1/2012 | Harrington et al. | |
| 2012/0022380 A1 | 1/2012 | Chernomorsky | |
| 2012/0024293 A1 | 2/2012 | Maguire et al. | |
| 2012/0143006 A1 | 6/2012 | Avitsian et al. | |
| 2012/0215198 A1 | 8/2012 | Cheney | |
| 2013/0060273 A1 | 3/2013 | Fogarty et al. | |
| 2013/0092171 A1* | 4/2013 | Sederstrom | A61M 16/04 128/207.15 |
| 2013/0112207 A1 | 5/2013 | Roth | |
| 2013/0190706 A1 | 7/2013 | Kleiner | |
| 2013/0211385 A1* | 8/2013 | Lazarus | A61M 1/87 604/540 |
| 2014/0033455 A1 | 2/2014 | Vazales et al. | |
| 2014/0041665 A1* | 2/2014 | Hwang | A61M 16/04 128/207.14 |
| 2015/0034078 A1* | 2/2015 | Sovndal | A61M 16/0488 128/200.26 |
| 2015/0101598 A1 | 4/2015 | Wang et al. | |
| 2015/0101611 A1 | 4/2015 | Wang | |
| 2015/0101612 A1 | 4/2015 | Wang | |
| 2015/0209239 A1* | 7/2015 | Salvino | A61L 29/14 604/101.05 |
| 2018/0126106 A1* | 5/2018 | Guan | A61M 16/0434 |
| 2019/0201662 A1* | 7/2019 | Lad | A61L 29/085 |

FOREIGN PATENT DOCUMENTS

| | | |
|---|---|---|
| CN | 203763616 U | 8/2014 |
| DE | 202009016034 U1 | 3/2010 |
| EP | 1889636 A1 | 2/2008 |
| WO | 9321816 A1 | 11/1993 |
| WO | 9640339 A1 | 12/1996 |
| WO | 2007130579 A2 | 11/2007 |
| WO | 2012087837 A1 | 6/2012 |
| WO | 2015042607 A1 | 3/2015 |

OTHER PUBLICATIONS

International Search Report and Written Opinion of the International Searching Authority, Patent Cooperation Treaty (Jan. 16, 2018), PCT/US2017/056393, 15 pgs.

International Search Report and Written Opinion of the International Searching Authority, Patent Cooperation Treaty (Jan. 28, 2015), PCT/US2014/059958, 13 pgs.

Kimberly-Clark Worldwide, Inc, Kimvent Closed Suction Systems, Date Retrieved Oct. 29, 2014, 4 pages.

Smiths Medical, SACETT Suction Above Cuff ET Tube, Date Retrieved Oct. 29, 2014, 9 pages.

Teleflex, Inc, Teleflex ISIS HVT, the First Convertible Endotracheal Tube, Date Retrieved Oct. 29, 2014, 2 pages.

* cited by examiner

200

SYSTEMS AND DEVICES FOR PREVENTING OCCLUSION OF A SUCTION LINE RESIDENT IN A MEDICAL DEVICE

RELATED APPLICATION

This application is a NON-PROVISIONAL of, and claims priority to, U.S. Provisional Patent Application No. 62/767,939 entitled "SPACER FOR SUCTION DEVICES AND SYSTEMS FOR USE WITH MEDICAL DEVICES" filed Nov. 15, 2018 which is incorporated by reference, in its entirety, herein.

TECHNICAL FIELD

This specification generally relates to the field of medical devices and, more specifically to devices that prevent occlusion of a suction line as may be deployed by and/or resident in a medical device such as a tracheal tube, a laryngeal mask airway, a tracheostomy tube, a laparoscopic tool, and a cystopic tool such as a urinary catheter.

BACKGROUND

Tracheal tubes with inflatable balloons with suction means are broadly known in the prior art. However, the suctioning means of such prior arts are inefficient with suctioning secretions above and around the balloon, therefore allowing secretions and/or pathogens to travel through the balloon and tracheal walls and into the airflow of the tracheal tube. In certain situations, the secretions/pathogens get aerosolized by the high velocity of the ventilated air traveling through the tracheal tube and into the patient's lungs. Aerosolized pathogens traveling at high velocity may send the pathogens deep into the lungs, which may cause ventilator associated pneumonia (VAP) as well as other diseases.

SUMMARY

Systems and devices for preventing occlusion of a suction line resident in a medical device are herein disclosed. One embodiment of the present invention utilizes a tube system that may include a tube that is flexible and hollow with a first open end and a second open end, a suction line configured to be coupled to a suction device that applies negative pressure to the suction line, a suction line port, and a spacer that extends from an exterior surface of the tube and is positioned proximate to the suction line port. The first open end of the tube may be configured to be coupled to an artificial ventilation device. The negative pressure created by the suction device may suck fluid from the trachea through the suction line port when the tube system is placed in a patient's trachea and the suction device is active.

The tube may further include an inflatable balloon affixed to, and circumferentially surrounding an exterior portion of the tube. The inflatable balloon may be positioned between the first open end and the second open end of the tube and may be inflated via an inflation line lumen coupled to an air supply.

The spacer may be configured and/or positioned to prevent occlusion of the suction line port and may be affixed to the tube via a bond, a sleeve, a clip, a strap, and/or a clamp. In some instances, the spacer may be flexible or otherwise deformable so as to, for example, adapt to a patient's anatomy and/or ease insertion of the tube system into a patient's trachea.

In some embodiments, the tube system may include a plurality of spacers positioned proximate to the suction line port. Additionally, or alternatively, the spacer(s) may extend longitudinally along a portion of a length of the tube. Additionally, or alternatively, the spacer(s) may extend circumferentially around a portion of a circumference of the tube.

In some embodiments, the spacer, or a portion thereof, may not touch the exterior surface of the tube and may, instead, extend above the exterior surface of the tube. For example, the portion of the spacer that does not touch the exterior surface of the tube may be flexible and may be configured to compress toward the exterior surface of the tube when a force is exerted thereon during, for example, insertion of the tube system into the trachea of a patient and/or when resident within the patient's trachea. Additionally, or alternatively, the spacer(s) may be coupled to the tube via an extension that extends between the spacer and the exterior surface of the tube. For example, the spacer may include a ring that extends circumferentially around a circumference of the tube and a plurality of extensions that extend between the ring and the exterior surface of the tube. Additionally, or alternatively, the tube system may include a first ring that extends circumferentially around a circumference of the tube that is positioned between the balloon and the suction line port and coupled to the tube via a first plurality of extensions that extend between the first ring and the exterior surface of the tube. In some cases, the tube system may further include a second ring that extends circumferentially around a circumference of the tube that is positioned between the suction line port and the second end of the tube and may be coupled to the tube via a second plurality of extensions that extend between the second ring and the exterior surface of the tube. An inner circumference of the first and/or second rings may be between 100% and 150% of an outer circumference of the tube. An outer circumference of the first and/or second rings may be between 100.1% and 200% of an outer circumference of the tube.

In some embodiments, the tube may further include an volume replacement channel that may be configured to introduce ambient air (or another substance flowing through volume replacement channel) into the patient's trachea such that, for example, a distance between the first and second ports of the volume replacement channel allows for ambient air (or another fluid) to flow into the first port and exit the second port. This may aid in the suction of air and fluid from the patient's trachea. In some instances, the volume replacement channel may include a first port positioned proximate to the inflatable balloon and a second port positioned near the second open end of the tube.

BRIEF DESCRIPTION OF THE FIGURES

The present invention is illustrated by way of example, and not limitation, in the figures of the accompanying drawings, in which:

FIGS. 3I and 3J provide front views of portions of exemplary tube systems like the exemplary tube systems, consistent with an embodiment of the present invention;

DETAILED DESCRIPTION

Medical devices like tracheal tubes, tracheostomy tubes, laryngeal mask airways, laparoscopic tools, and a cystopic tools such as urinary catheters may include a suction line that may be used to evacuate air, liquid (e.g., secretions), and/or other materials from a patient undergoing a medical procedure using one of these medical devices. Evacuation of the air, liquid, or other materials may improve the functionality of the medical device and/or may decrease irritation and/or risk of disease or complications for the patient undergoing a procedure using the medical device. For example, if the liquid and/or other materials are not evacuated from an intubated patient's trachea then, they may begin to pool in the patient's trachea. These pooling secretions may, for example, interfere with the operation of a tracheal tube or tracheostomy tube because, for example, liquid, tissue, and/or foreign matter within a patient's trachea or throat that may occlude a suction line port by, for example, pressing against a suction line port and/or forming a seal around the suction line port thereby preventing the application of negative pressure (i.e., suction) to the patient's trachea.

Exemplary medical devices, or tube systems, disclosed herein may include one or more spacers affixed to an external surface of tube (e.g., tracheal or tracheostomy) or other portion of the medical device. The spacers may be arranged and/or configured to prevent occlusion of the suction line port by, for example, preventing large (i.e., larger than a portion of a diameter of the suction line port) pieces of material, or bodies from being sucked into, and thereby blocking, the suction line port. In some embodiments, spacers may be of differing height and incorporate channels for the passage of air and/or fluid.

Often times, the spacers are smooth and form a smooth seal with the tube of, for example, a tracheal tube and/or tracheostomy tube system. The spacers may provide space (e.g., 0.025 cm-1 cm) between the tube and a patient's tissue (e.g., trachea or airway) by pushing the tissue away from the tube and/or a suction line port of the tube. In this way, the spacer may prevent patient's tissue from pushing against, or otherwise occlude, the suction line port thereby leaving space in the trachea for fluid and air to be sucked into the suction line port upon application of negative pressure thereto.

In some embodiments, the spacers may be radio opaque so that they appear on, for example, an X-ray image of the patient's tissue (e.g., trachea). Often times the spacers and/or medical devices (tracheal tubes, tracheostomy tubes, etc.) are compatible with medical imaging technologies such as magnetic resonance imaging (MRI) and, as such, may not include any significant metal portion.

Figure 1A:
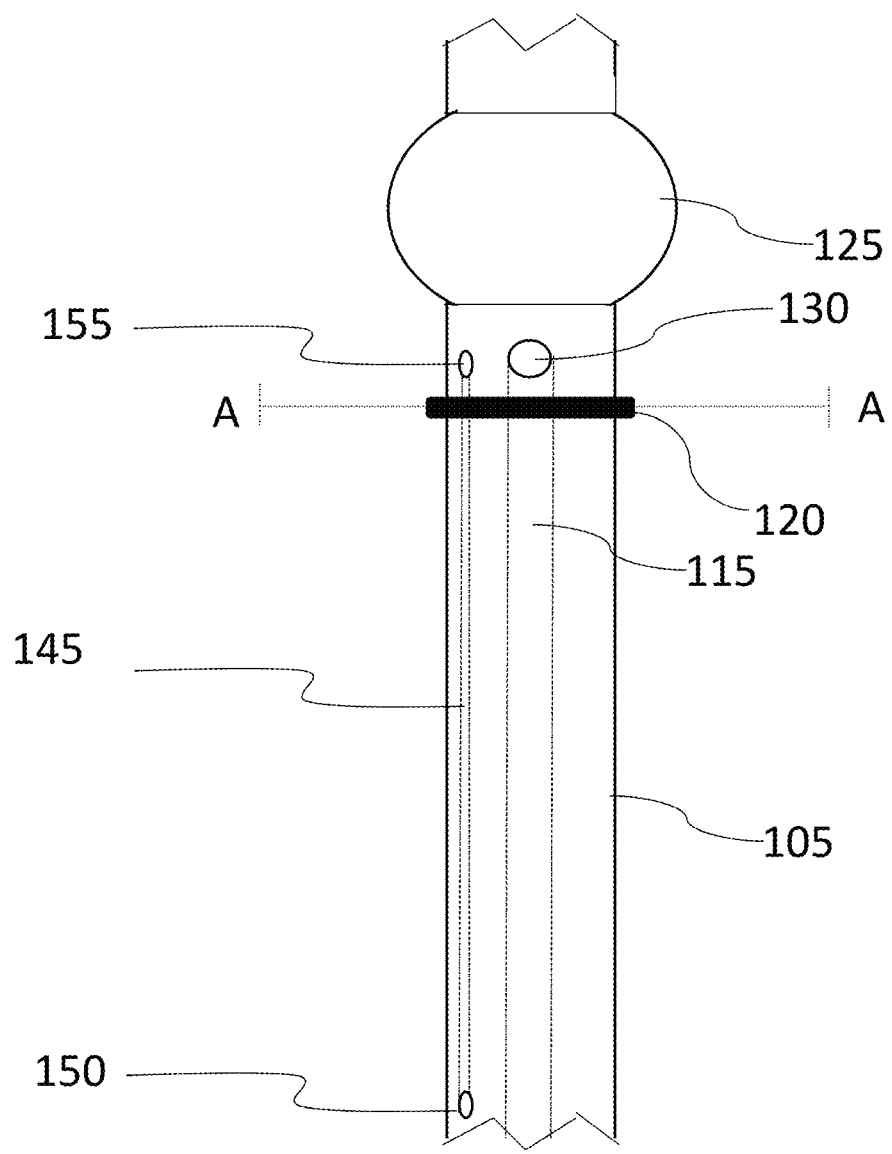
FIG. 1A provides a front view of a portion of an exemplary tube system, consistent with an embodiment of the present invention.

FIG. 1A provides a front view of a portion of an exemplary tube system 100 that includes a tube 105, a suction line 115 that extends down a portion of tube 105, a spacer 120, an inflatable balloon 125, and a suction line port or orifice 130. Tube system 100 may be a portion of, for example, a tracheal tube system and/or a tracheostomy tube system. Tube 105 may be configured to allow air or other gases provided by an artificial ventilation device (coupled to an end of tube 105) to flow through tube 105 into the lungs of an intubated (with tube system 100) patient. Inflatable balloon 125 may be inflated via air or another gas passing through an inflation line lumen (not shown) that is coupled to an air supply.

Optionally, in some embodiments, tube system 100 may include a communication line 145 with a first port 150 and a second port 150. Tube system 100 may be configured so that first port 150 is outside of an intubated patient's trachea. Communication line 145 may be configured to have a lumen along its length that allows for the passage of, for example, a material (e.g., gas, chemicals, medications, and/or fluid) therethrough through passive (e.g., exchange of ambient air) or active (e.g., an injection) means. The material may enter the first port 150 and exit the second port 155 and may thereby enter a subglottic region of an intubated patient.

Inflatable balloon 125 may be positioned between a first end and a second end of tube 105 and may circumferentially surround portion of tube 105. Inflatable balloon 125 may remain un-inflated, or deflated, until tube system 100 is inserted into a patient's trachea and positioned appropriately therein. Once tube system 100 is properly positioned within the patient's trachea, inflatable balloon 125 may be inflated using air, or another gas, passed through an inflation line (not shown) from an inflation pump (not shown). Inflating inflatable balloon 125 to a desired degree of inflation while positioned within the patient's trachea may serve to stabilize tube system's 100 positioning within the patient's trachea/throat and may also serve to prevent an unintentional, or undesired, gas and/or liquid exchange between the patient's lungs and the patient's trachea and/or outside environment while the patient is intubated.

Spacer 120 may be configured to position tracheal tissue of an intubated patient and/or other foreign matter (e.g., fluid or solids) present in the trachea away from the surface of tube 105 by, for example, exerting a pressure or force thereon. In this way, spacer 120 may serve to prevent, or reduce, occlusion of suction line port 130 by the tracheal tissue and/or foreign matter. Spacer 120 may be any appropriate shape or combination of shapes including, but not limited to, a circular ring, a semi-circular portion of a ring, and/or an extension projecting from an exterior surface of tube 105. The extension may be, for example of a circular, semi-circular, triangular, linear, and/or rectangular shape. In some instances, a plurality of spacers 120 may be present in system 100. Spacer 120 may have a solid or hollow cross section. At times, spacer 120 may be flexible but, this may not always be the case. Spacer 120 may be made from any appropriate material including, but not limited to, silicon, plastic, and vinyl. Spacer 120 may be an integrated part (i.e., manufactured as, for example, tube 105 is extruded from a fabrication device) of tube system 100 and/or may be affixed to tube 105 following its manufacture via, for example, a chemical, mechanical, and/or heat bonding process. In some instances, spacer 120 may incorporate a smooth tissue facing side to prevent abrasion of an intubated patient's tissue.

Figure 1B:
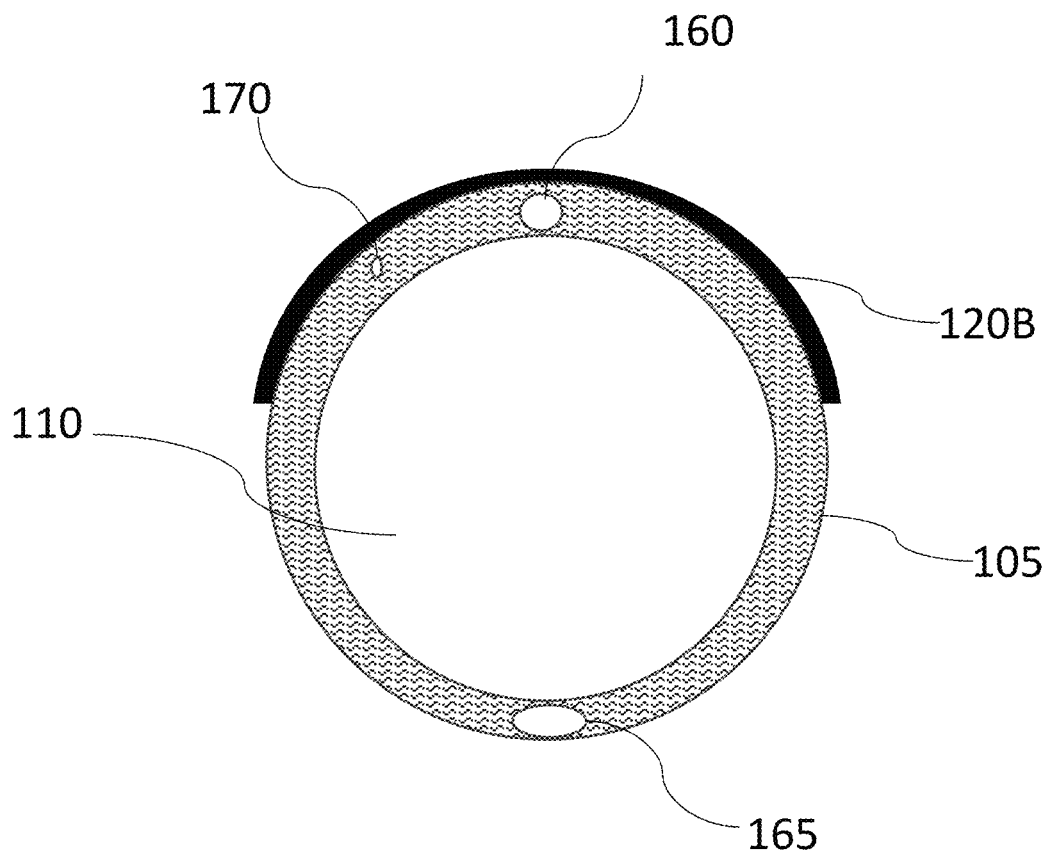
FIGS. 1B-1E provide a cross-sectional views of exemplary tube systems, consistent with embodiments of the present invention.
Figure 1C:
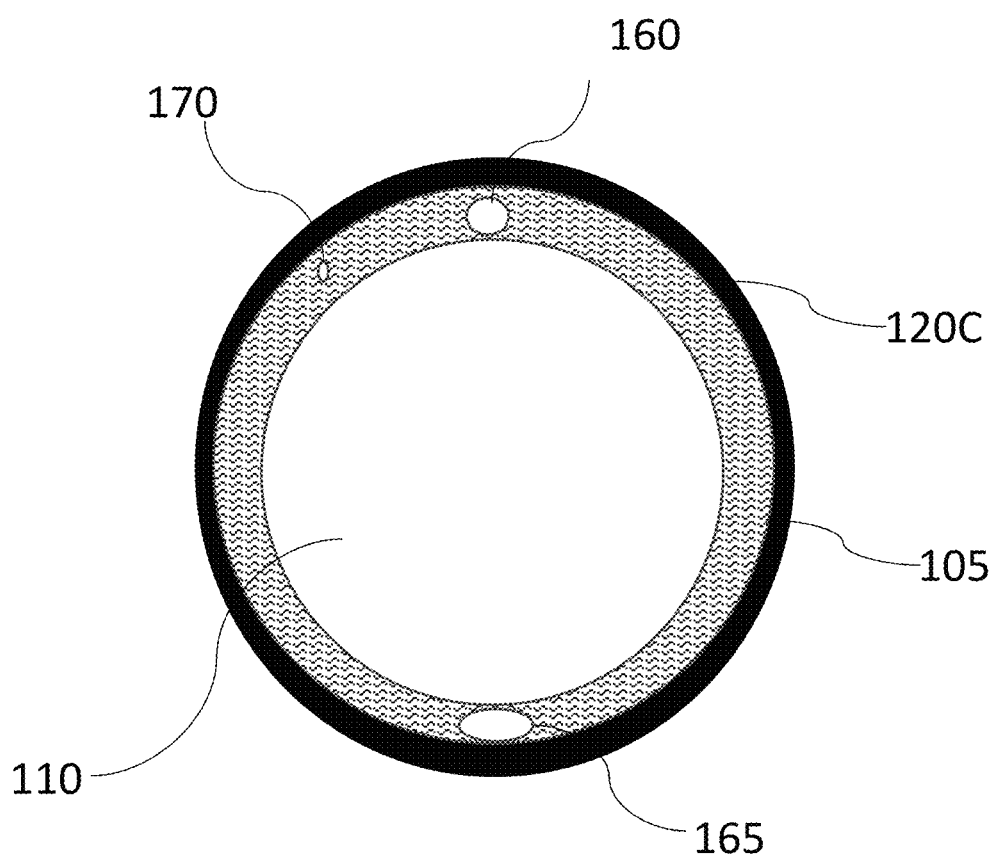
Figure 1D:
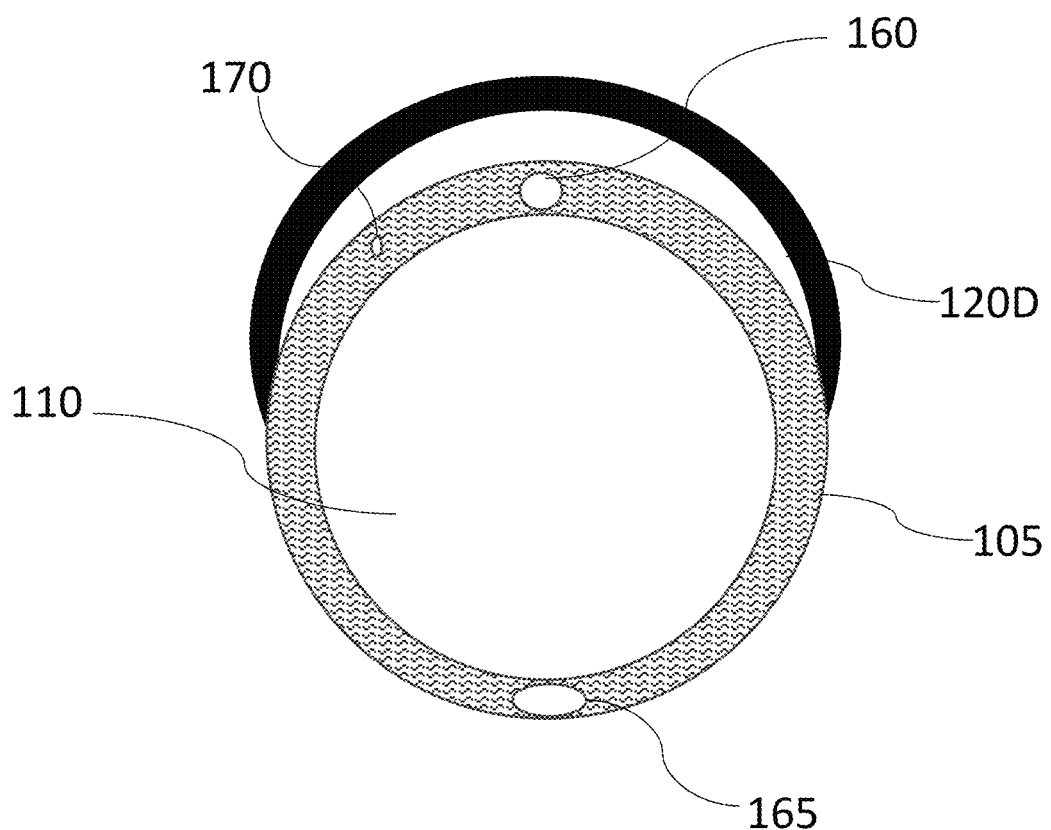
Figure 1E:
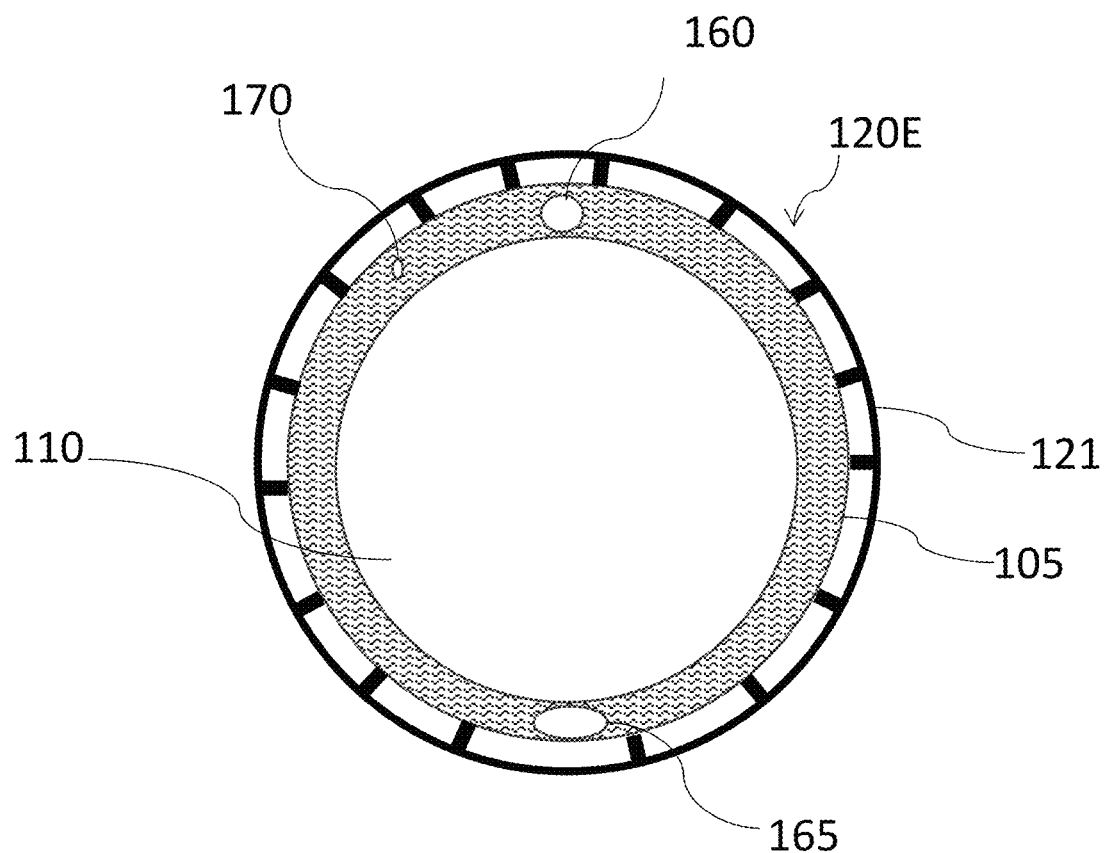
Figure 1F:
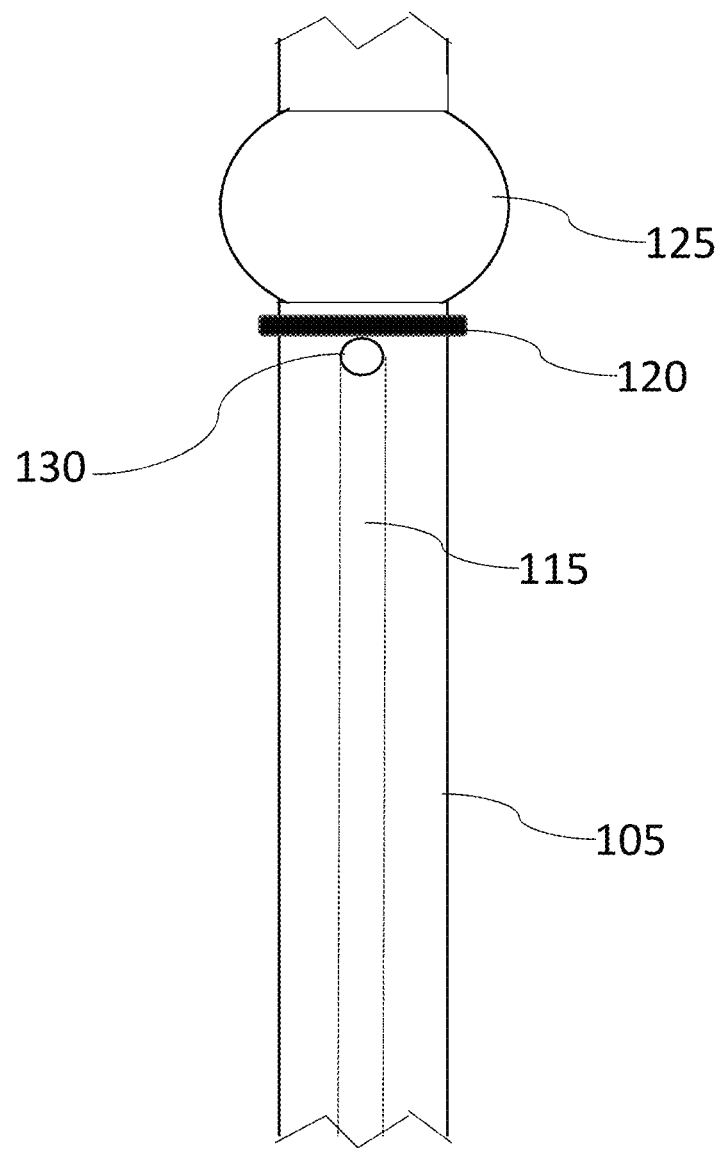
FIGS. 1F-1H provide front views of portions of exemplary tube systems, consistent with embodiments of the present invention.

On some occasions, an exemplary spacer 120, or a portion thereof, may be bonded directly to an exterior surface of tube 105 so that portion of an exterior surface of the exemplary spacer is in contact with the exterior surface of tube 105 (see e.g., FIGS. 1B and 1C) and, in other instances, a space (e.g., open area) between spacer 120 and tube 105 may be present (see e.g., FIGS. 1D and 1E). In some circumstances, spacer 120 may be fixed in its configuration and/or position and, in other circumstances, it may be movable and/or deformable. Spacer 120 may have a cross-sectional width or diameter within the range of 0.1-1.5 cm so that when positioned on, or adjacent to, tube 105, it extends 0.1-1.5 cm above the exterior surface of tube 105.

Spacer 120 may be positioned adjacent to and/or above suction line port 130. In some embodiments, a spacer 120 may include one or more mechanisms (e.g., curves, notches, and/or openings) that assist with the flow of materials (e.g., liquids or solids) into suction line port 130 by, for example, redirecting the negative pressure supplied by the suction line and/or channeling fluids and other material into the suction line opening.

In some embodiments, spacer 120 may act as a sieve or screen that prevents relatively large particles from entering (and potentially occluding) suction line port 130 and/or suction line 115. Spacer 120 may cover and/or be proximate to all or a portion of suction line port 130.

FIGS. 1B-1E provide cross-sectional views of different embodiments of tube system 100, 100A, 100B, 100C, 100D, respectively, taken at position A (shown in FIG. 1A with dashed lines), that employ different exemplary spacers 120B-120E, respectively. Also shown in FIGS. 1B-1E are a central lumen 110 for tube 105 as well as a suction line lumen 160, an inflation line lumen 165, and a communication line lumen 170. Suction line lumen 160 serves as a lumen through which air, liquid, and other materials may be sucked out of an intubated patient's trachea and inflation line 135 is configured to allow the passage of air therethrough to inflate and/or deflate inflatable balloon 125.

Spacer 120B of FIG. 1B is curved in a substantially semi-circular fashion with a shape that aligns with the curved shape of the exterior surface of tube 105 and wraps around a portion of tube 105. Spacer 120B may be configured to and/or positioned on tube 105 to align with a posterior portion of an intubated patient's trachea so that it is present in a place where fluid is more likely to pool in the trachea due to gravitational force on the fluid. Spacer 120C of FIG. 1C is circular, or ring-like, in shape and encircles the circumference of tube 105.

In some embodiments, spacer 120 may be bonded to tube 105 in one or more locations and a portion of these spacers 120 may extend away from (e.g., not abut) an exterior surface of tube 105. For example, spacer 120D of FIG. 1D is substantially semi-circular in shape and is bonded to tube 105 on the left and right side of tube 105 (as shown in FIG. 1D) so that a portion of spacer 120D extends away from a portion of the exterior surface of tube 105 with a space therebetween. In some embodiments, spacer 120D may be flexible so that it may be, for example, compressed toward tube 105 in some circumstances (e.g., when inserting tube system 100 into a patient and/or residing within an intubated patient).

In another example, a spacer 120E of FIG. 1E has an outer ring 121 that is substantially circular in shape. Outer ring 121 is bonded to tube 105 at multiple locations via a plurality of extensions that extend between outer ring 121 and an exterior surface of tube 105 as shown in FIG. 1E so that there is empty space between outer ring 121 and tube 105. Outer ring 121 and/or the extensions connecting outer ring 121 to tube 105 may be flexible in order to, for example, ease insertion of system 100 into a patient's trachea and/or adapt to the anatomy of the patient's tracheal walls. On some occasions, the extensions connecting outer ring 121 to tube 105 may act as a sieve or screen that prohibits suctioning of a particle above a particular size into suction line port 130.

Figure 1G:
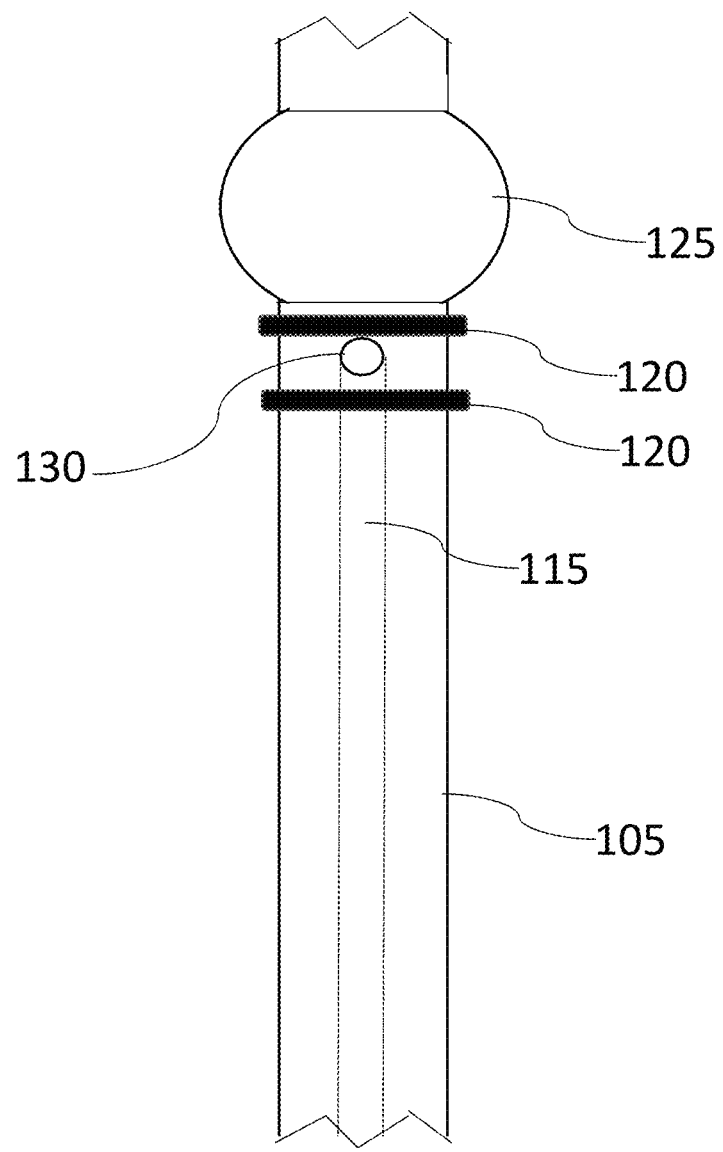
Figure 1H:
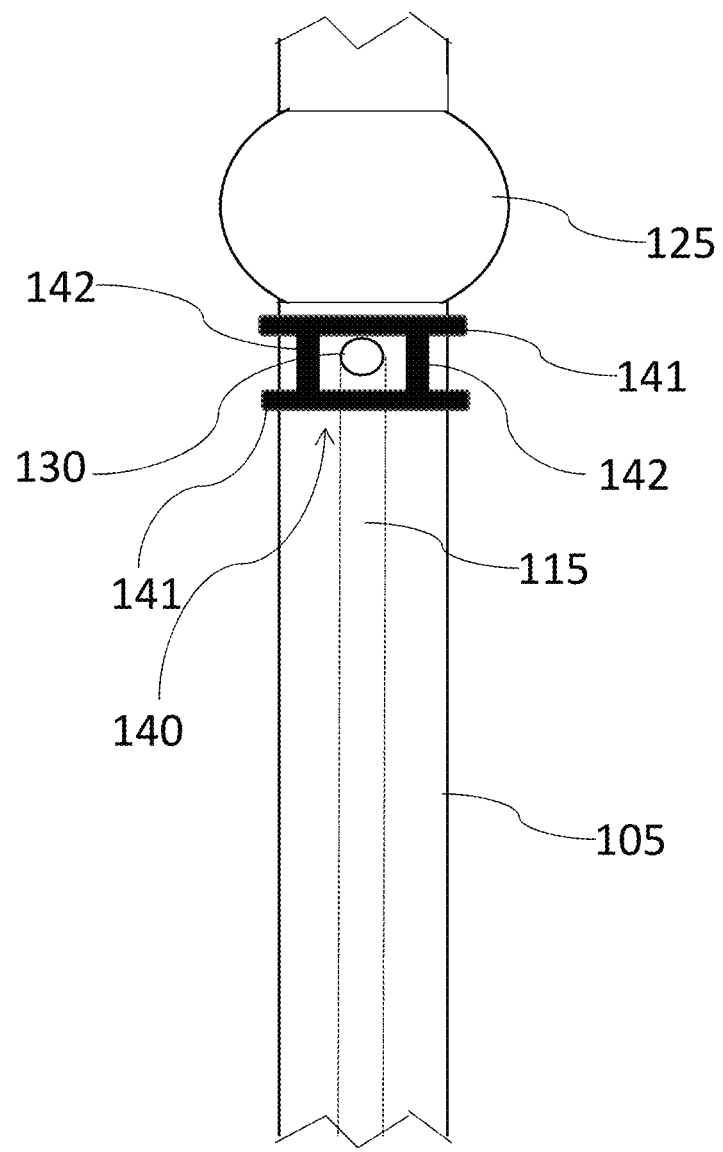

A spacer such as spacers 120, 120A, 120B, 120C, 120D, and/or 120E may be positioned at any appropriate location on tube system 100. For example, spacer 120, 120A, 120B, 120C, 120D, and/or 120E may be positioned above suction line port 130 (i.e., between suction line port 130 and an end of tube system 100 configured to be positioned outside the body when used) as shown in FIG. 1A. In another example, a spacer 120 may be positioned below suction line port 130 so that it is positioned between suction line port 130 and an upper portion of inflatable balloon 125 as shown in FIG. 1H which illustrates an exemplary tube system 101 that may be a portion of, for example, a tracheal tube system and/or a tracheostomy tube system. Alternatively, a tube system 102 may include two spacers 120 with a first spacer 120 positioned above suction line port 130 and a second spacer positioned below suction line port 130 as shown with exemplary tube system 102 of FIG. 1G. Tube system 102 may be a portion of, for example, a tracheal tube system and/or a tracheostomy tube system.

FIG. 1H provides an additional exemplary tube system 103 that includes an exemplary spacer 140. Tube system 103 may be a portion of, for example, a tracheal tube system and/or a tracheostomy tube system. Spacer 140 includes two rings 141 that encircle tube 105 that are connected to one another by a plurality of extensions 142. Rings 141 are substantially parallel to one another and are substantially perpendicular to tube 105. Extensions 142 are substantially perpendicular to rings 141 and substantially parallel to tube 105. Extensions 142 may be positioned so as to not interfere with suction line port. For example, as shown in FIG. 1H, extensions 142 are positioned on the left and right sides of suction line port 130 and connect rings 141 to form a shape that looks like a horizontally-oriented extension ladder.

Figure 2A:
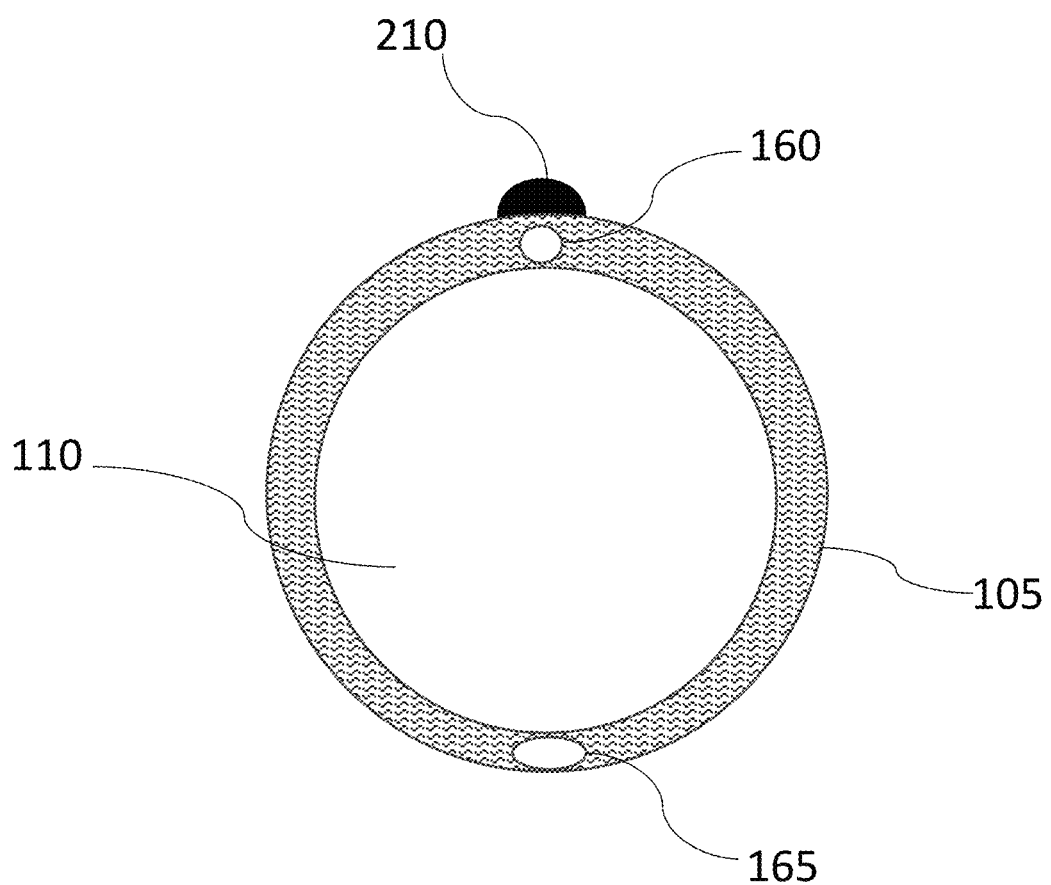
FIG. 2A provides a cross-section view of another exemplary tube system, consistent with an embodiment of the present invention.
Figure 2B:
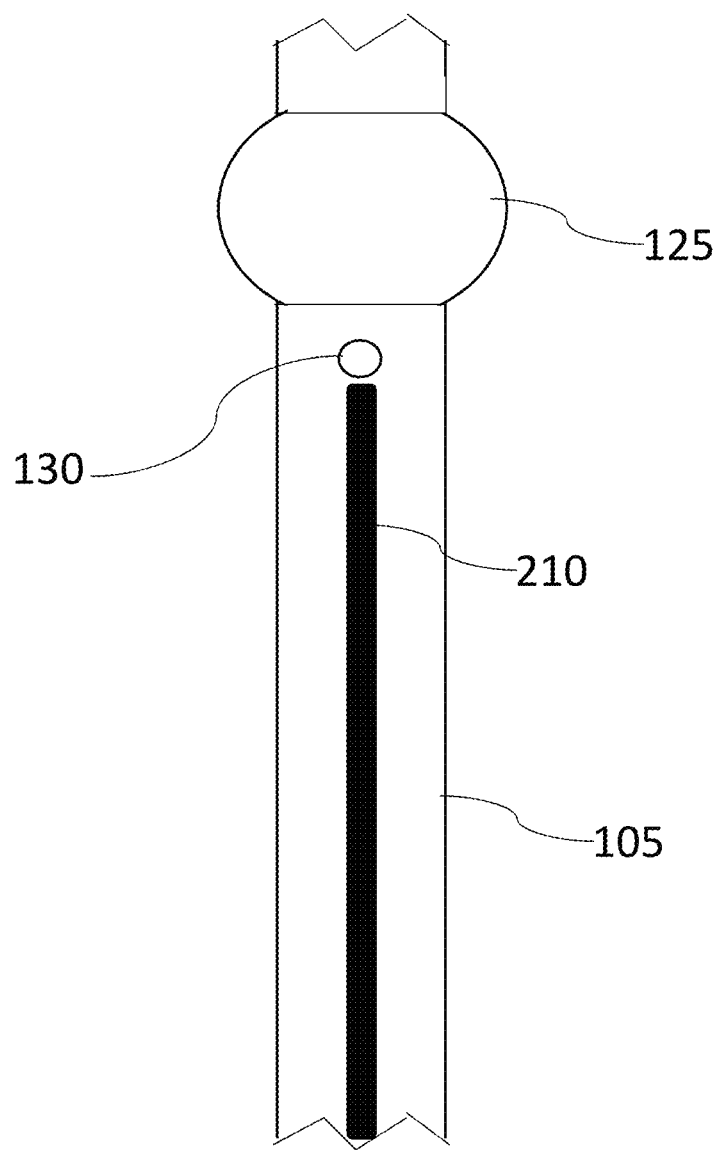
FIG. 2B provides a side view of the exemplary tube system of FIG. 2A, consistent with an embodiment of the present invention.

FIG. 2A shows a cross-section view and FIG. 2B shows a front view of another exemplary tube system 200 that includes a longitudinal spacer 210 that is positioned on, and extends longitudinally along a length of, a portion of tube 105 as shown in FIG. 2B, central lumen 110 for tube 105, suction line lumen 160, inflatable balloon 125, suction line port 130, and inflation line lumen 165. Tube system 200 may be a portion of, for example, a tracheal tube system and/or a tracheostomy tube system. Inflatable balloon 125 may be inflated via air or another gas passing through an inflation line lumen (not shown) that is coupled to an air supply.

Longitudinal spacer 210 may be molded as part of the manufacturing process (e.g., extrusion of tube 105 including longitudinal spacer 210) for tube system 200. Additionally, or alternatively, longitudinal spacer 210 may be affixed to an exterior surface of tube 105 via a chemical, mechanical, and/or thermal bonding process. Longitudinal spacer 210 may have any appropriate cross-sectional shape including, but not limited to, circular, oval, square, hexagonal, and trapezoidal. Longitudinal spacer 210 may be posited so that it acts prevent, or reduce, occlusion of suction line port 130. Although longitudinal spacer 210 is show as a continuous spacer, this need not always be the case. In some instances, longitudinal spacer 210 may include an array of multiple longitudinal spacers 210 arranged around the exterior surface of tube 105 in a linear, circular, and/or spiral pattern. In some embodiments, tube system 200 may include two or more longitudinal spacers 210 positioned on an exterior surface of tube 105. For example, a first longitudinal spacer 210 may be positioned on a left side of a suction line port and a second longitudinal spacer 210 may be positioned on a right side of suction line port 130. In this way, the two longitudinal spacers 210 may prevent blockage of suction line port 130 by a foreign object being sucked therein.

Figure 3A:
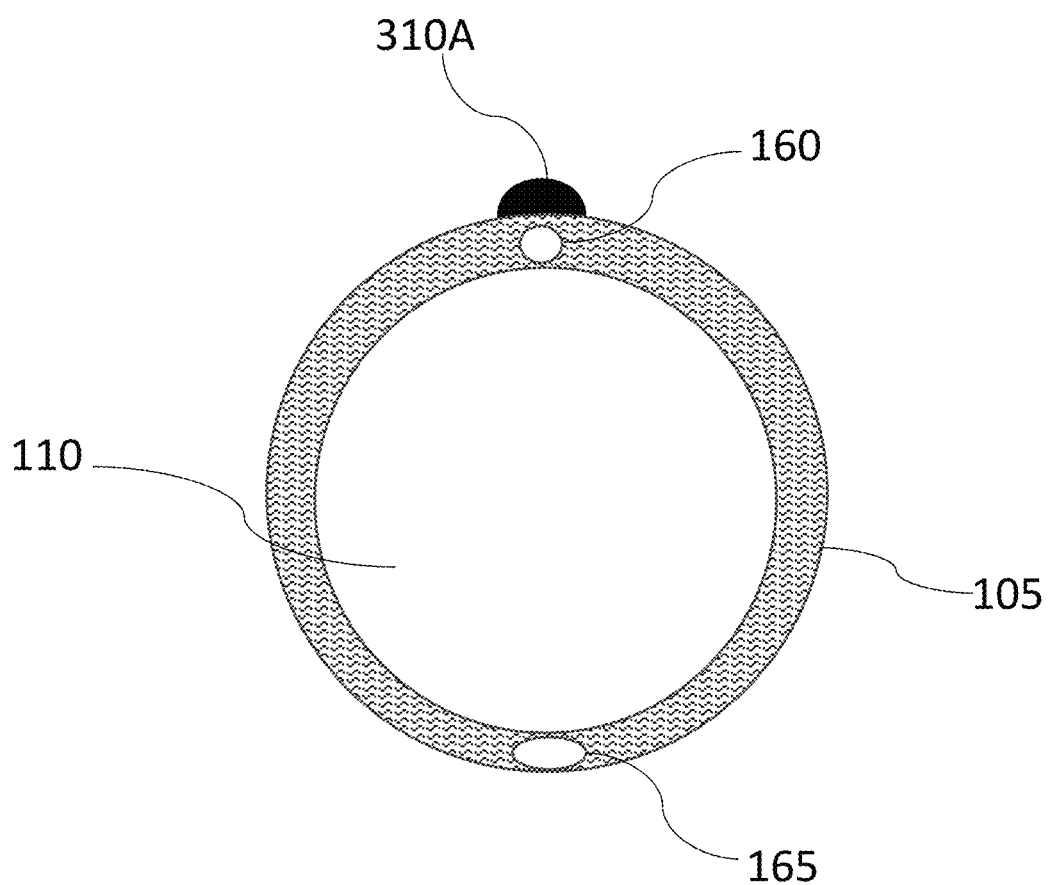
FIGS. 3A-3F show cross-section views of different embodiments of exemplary tube systems, consistent with embodiments of the present invention.
Figure 3B:
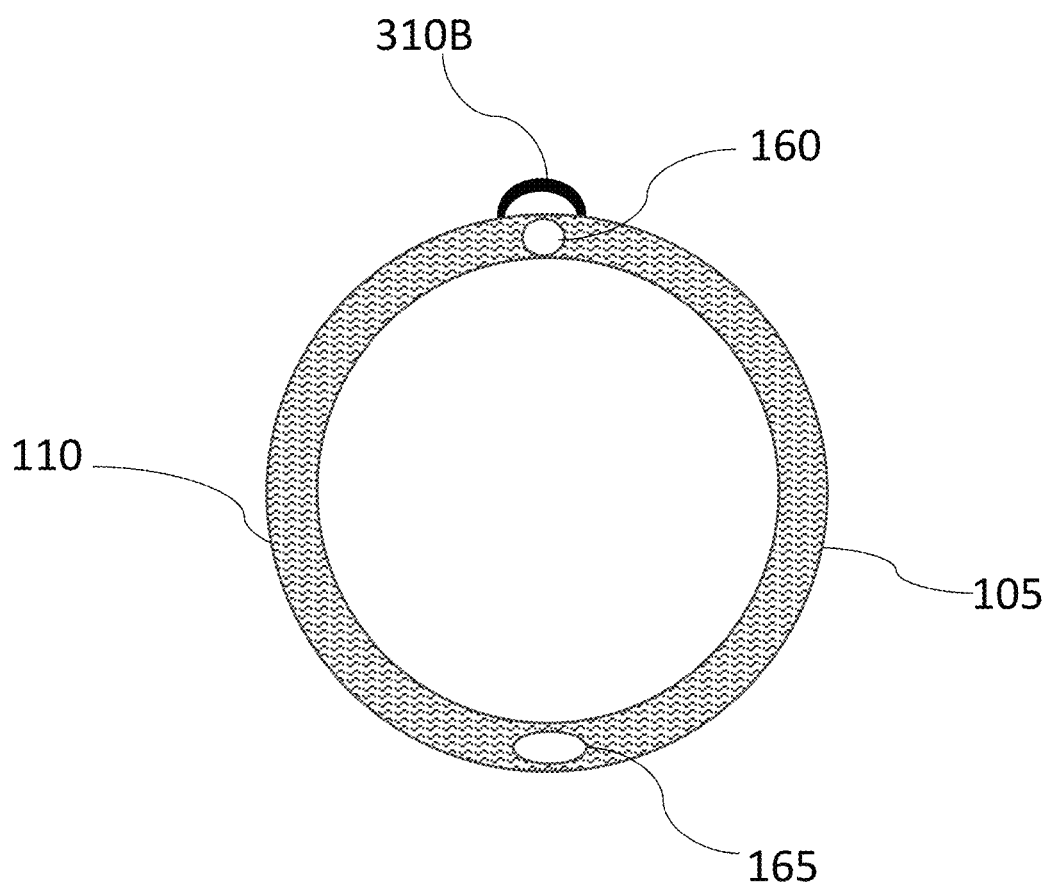
Figure 3C:
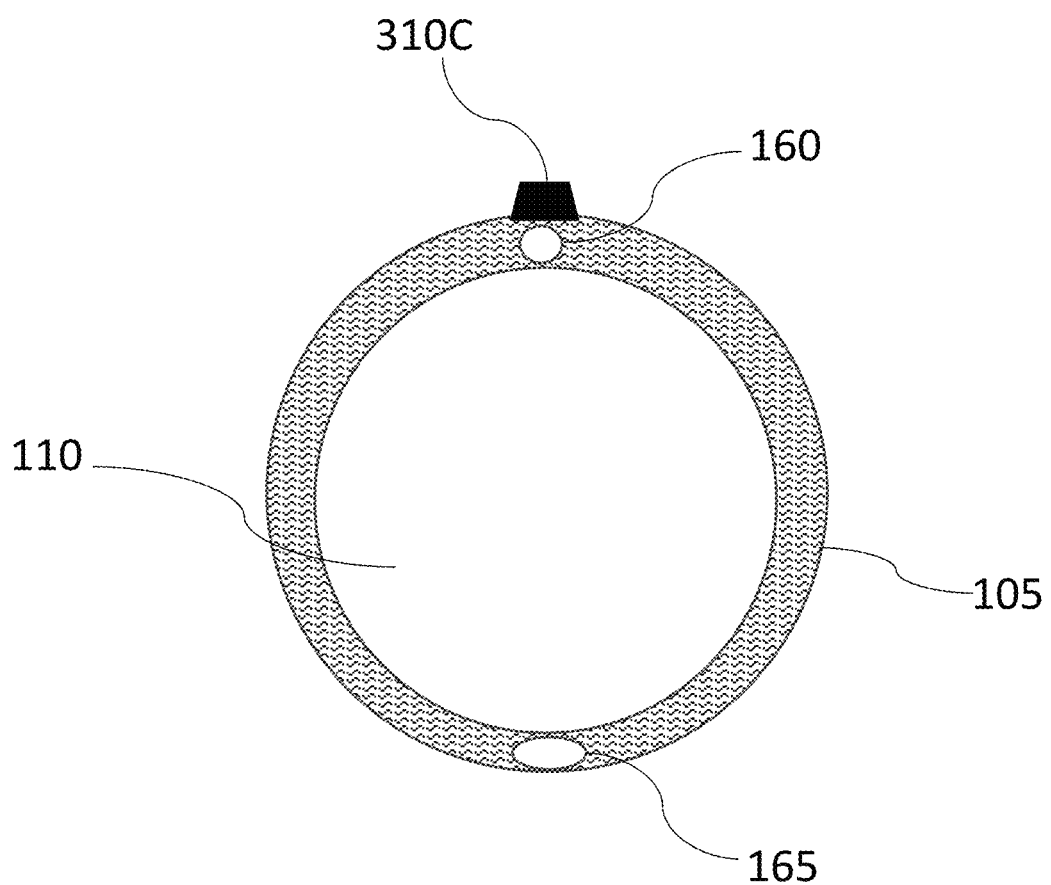
Figure 3D:
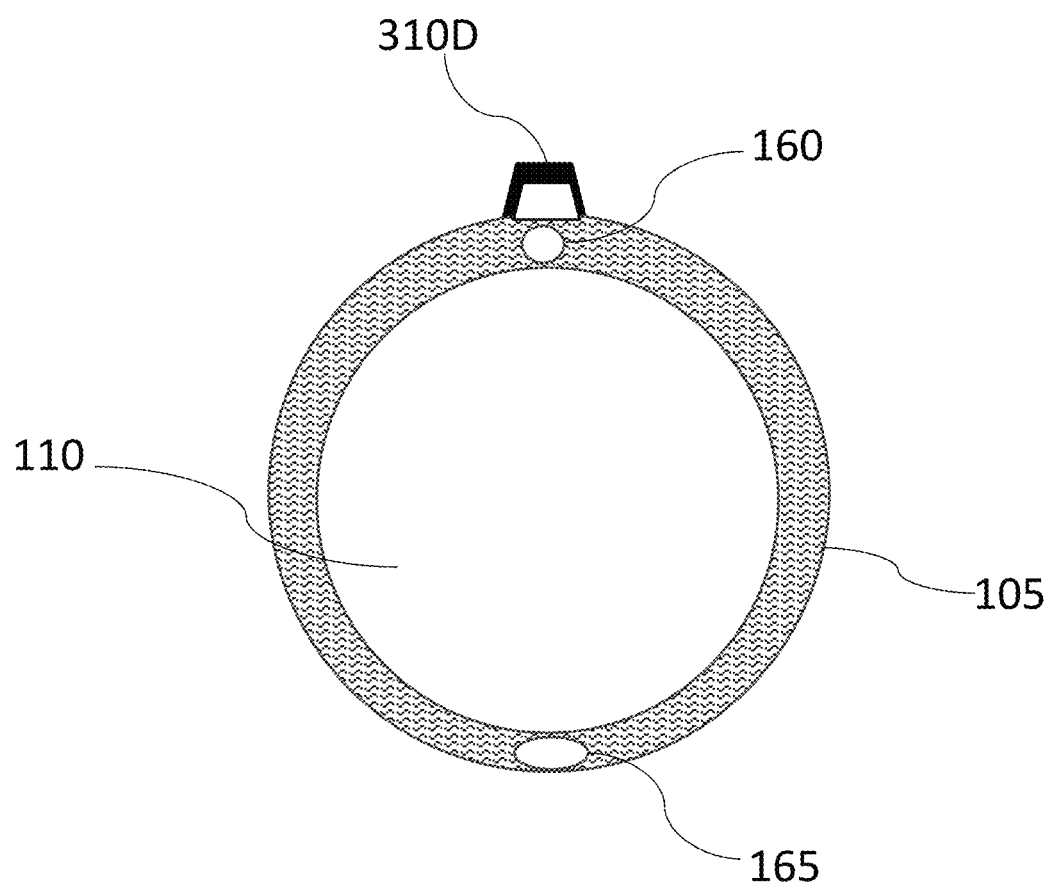
Figure 3E:
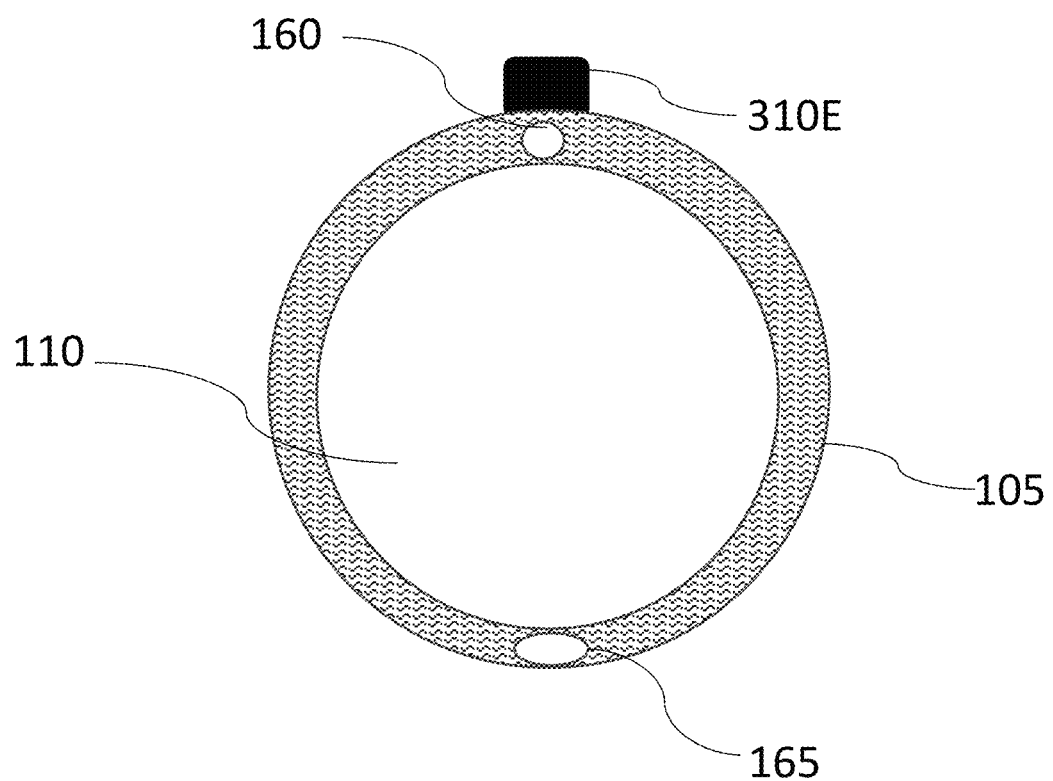
Figure 3F:
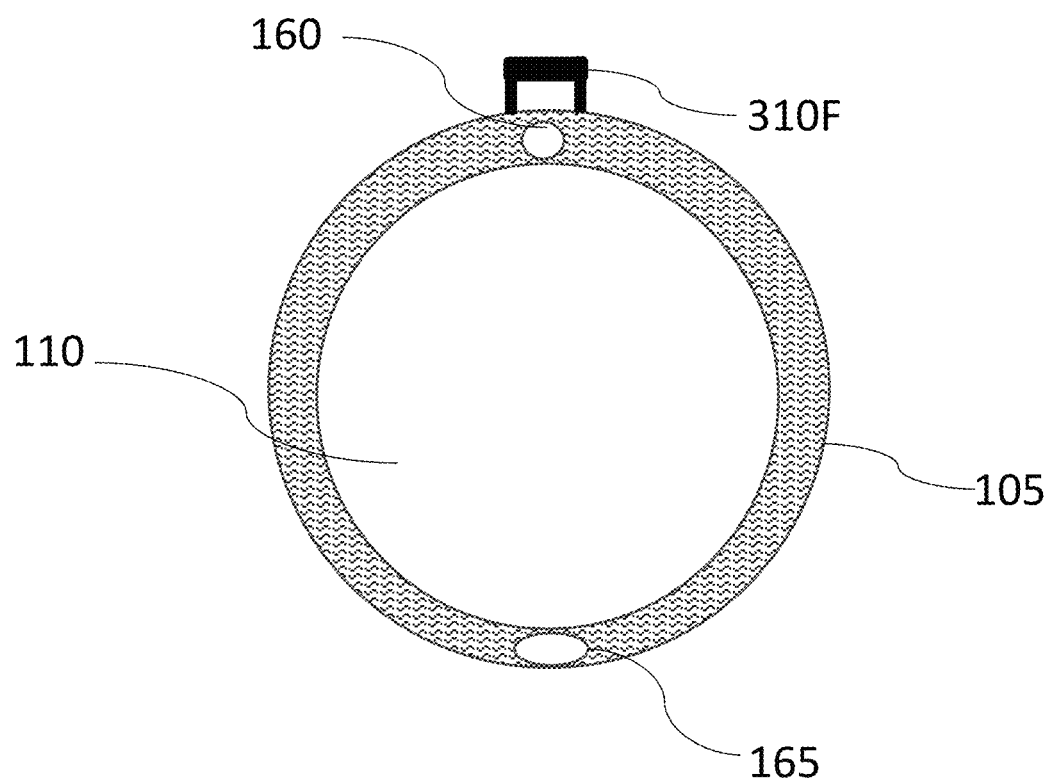
Figure 3G:
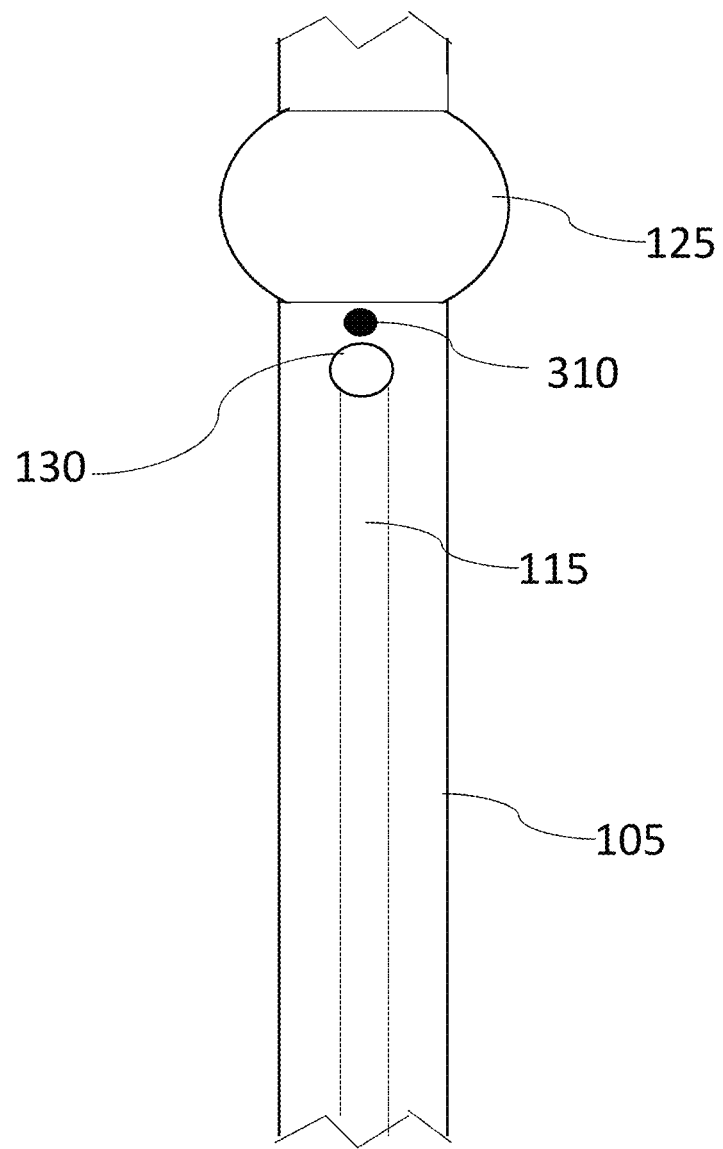
FIGS. 3G and 3H provide front views of portions of exemplary tube systems like the exemplary tube systems shown in FIGS. 3A-F, consistent with an embodiment of the present invention.
Figure 3H:
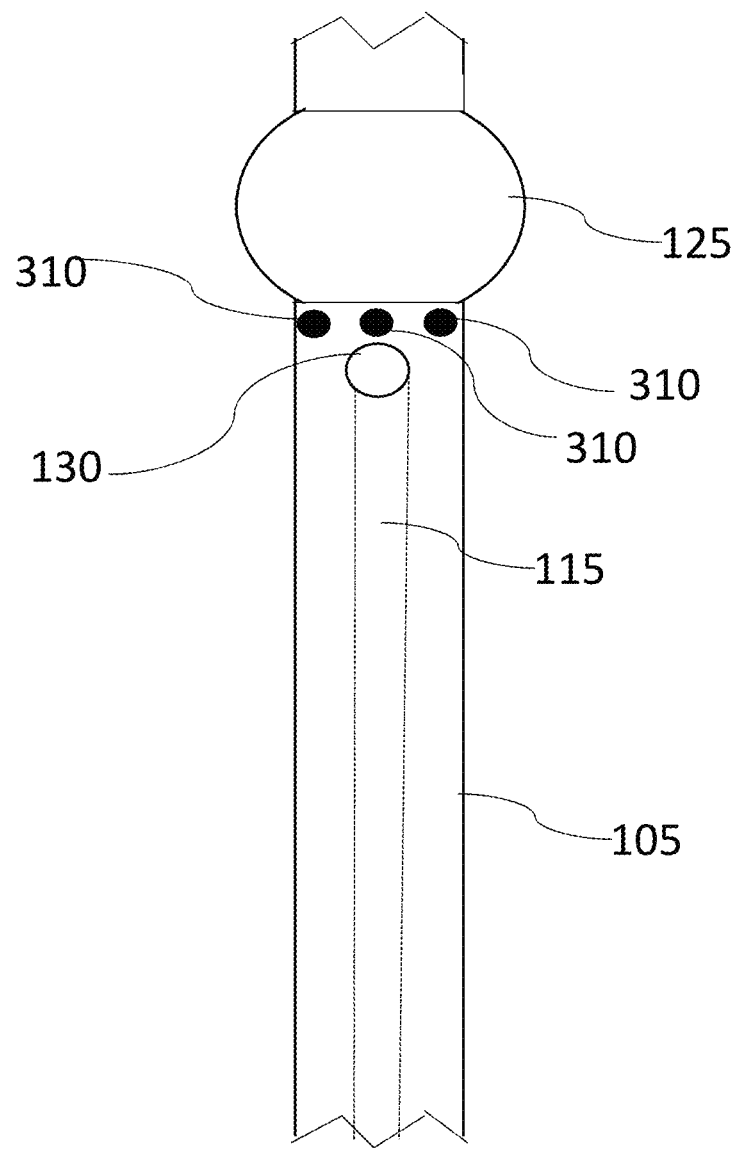
Figure 31:
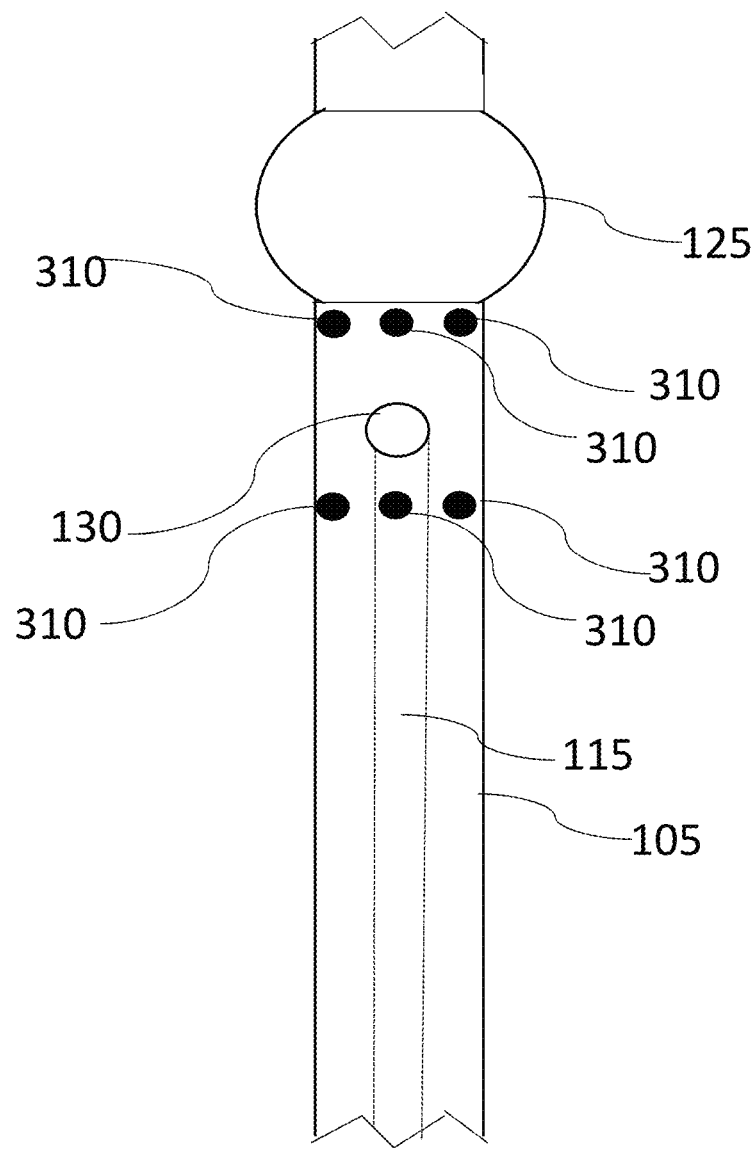

FIGS. 3A-3F show cross-section views of tube systems 300A, 300B, 300C, 300D, 300E, and 300F, respectively and FIGS. 3G and 3H show a side view of exemplary tube systems 300A, 300B, 300C, 300D, 300E, and 300F, 301, 302, and 303. Tube systems 300A, 300B, 300C, 300D, 300E, and 300F, 301, 302, and 303 include one or more spacers 310 positioned on and extending from an external surface of tube 105. In some cases, spacers 310 may resemble dimples. At times, spacers 310 may be flexible, compressible, or otherwise deformable. Tube systems 300A, 300B, 300C, 300D, 300E, and 300F, 301, 302, and 303 may be a portion of, for example, a tracheal tube system and/or a tracheostomy tube system.

One or more spacers 310 may be positioned proximate to suction line port 130. Tube systems 300, 301, 302, and 303 also include tube 105, central lumen 110 for tube 105, suction line lumen 160, inflatable balloon 125, suction line port 130, and inflation line lumen 165. In some embodiments, spacer(s) 310 may be flexible and/or deformable. Inflatable balloon 125 may be inflated via air or another gas passing through an inflation line lumen (not shown) that is coupled to an air supply.

Spacers 310 may be positioned on an exterior surface of tube 105 proximate to suction line port 130 in order to, for example, prevent, or reduce a likelihood of, occlusion of suction line port 130. Spacers 310 may be of any appropriate shape including, but not limited to, circular, oval, square, hexagonal, and trapezoidal and may be solid or hollow. For example, FIG. 3A provides a tube system 300A with a semi-circularly-shaped spacer 310A that is solid and FIG. 3B provides a tube system 300B with a semi-circularly-shaped spacer 310B that is hollow; FIG. 3C provides a tube system 300C with a trapezoid-shaped spacer 310C that is solid and FIG. 3D provides a tube system 300D with a trapezoid-shaped spacer 310D that is hollow; FIG. 3E provides a tube system 300E with a rectangularly-shaped spacer 310E that is solid and FIG. 3F provides a tube system 300F with a rectangularly-shaped spacer 310F that is hollow.

Figure 3J:
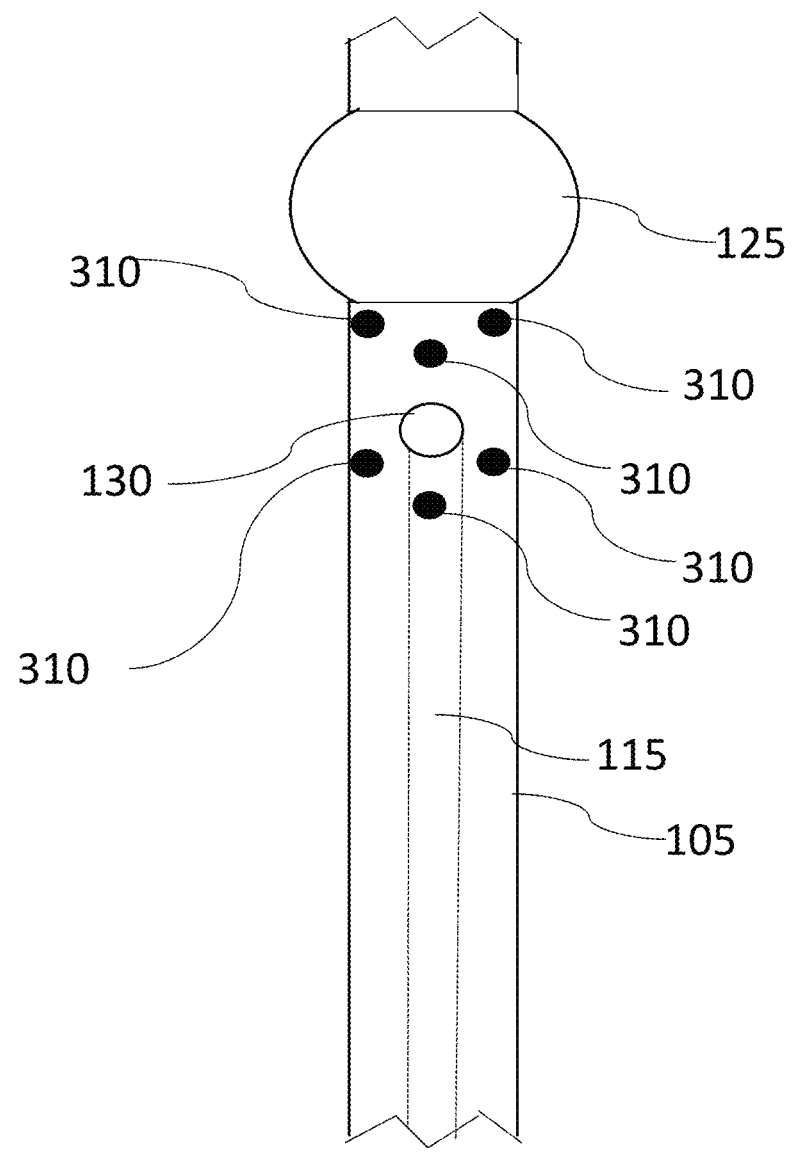

In the embodiments of FIGS. 3A-3F, tube systems 300A-300F include a single spacer 310A, 310B, 310C, 310D, 310E, or 310F, respectively. FIGS. 3H, 3I, and 3J, illustrate tube systems 301, 302, and 303, respectively, that include a plurality of spacers 310 (which may resemble, for example, spacers 310A, 310B, 310C, 310D, 310E, and/or 310F). In some instances, the array of spacers 310 may extend wholly around the circumference of tube 105 and, in other instances, the array of spacers 310 may extend around a portion (e.g., 30%, 50%, 75%, etc.) of the circumference of tube 105. In the example of tube system 301 shown in FIG. 3H, tube system 301 includes a plurality of spacers 310 arranged in a line that is substantially perpendicular to tube 105 and positioned between the upper portion of inflatable balloon 125 and suction line port 130. In the example of tube system 302 shown in FIG. 3I, tube system 302 includes a plurality of spacers 310 arranged in two lines that are substantially perpendicular to tube 105 with a first line of spacers 310 being positioned below suction line port 130 (i.e., between the upper portion of inflatable balloon 125 and suction line port 130) and a second line of spacers being positioned above suction line port 130. In the example of tube system 303 shown in FIG. 3J, tube system 303 includes a plurality of spacers 310 arranged in two zig-zag-like lines that are substantially perpendicular to tube 105 with a first zig-zag line of spacers 310 being positioned below suction line port 130 (i.e., between the upper portion of inflatable balloon 125 and suction line port 130) and a second zig-zag line of spacers being positioned above suction line port 130.

Figure 4A:
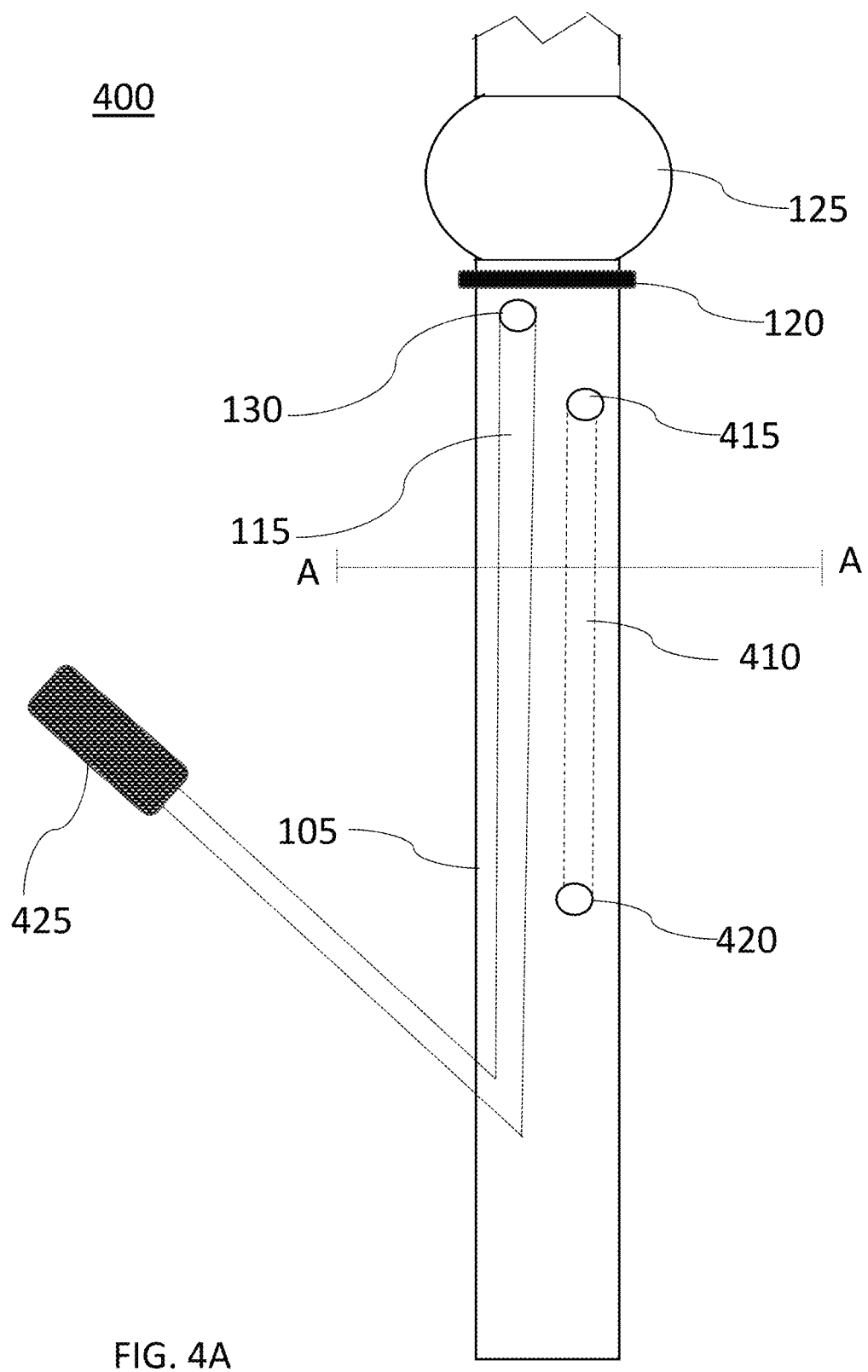
FIG. 4A provides side view of a portions of exemplary tube systems like the exemplary tube systems shown in FIGS. 3A and 3B, consistent with an embodiment of the present invention.
Figure 4B:
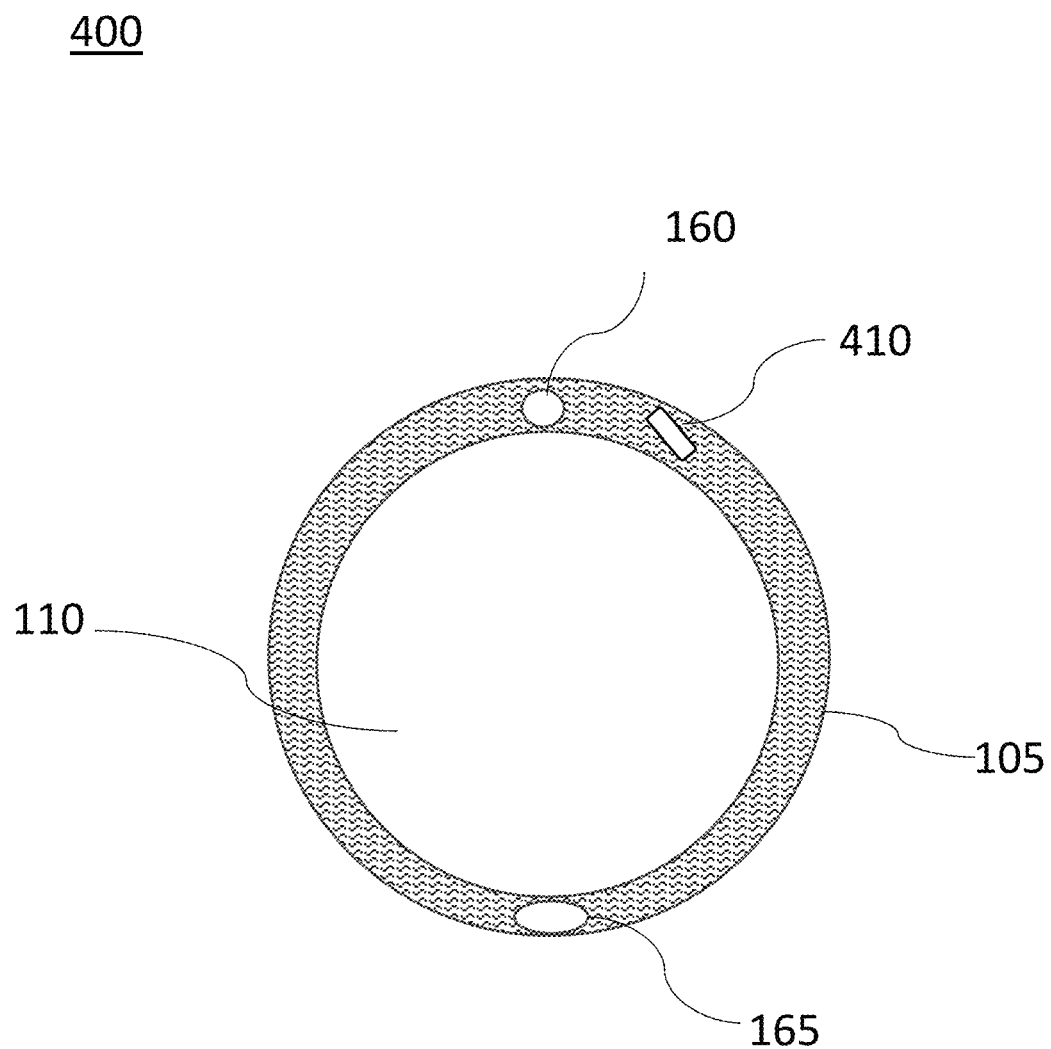
FIG. 4B shows a cross-section view of the embodiment of the exemplary tube system shown in FIG. 4A, consistent with an embodiment of the present invention.

FIGS. 4A and 4B show a tube system 400 that includes an volume replacement channel 410 with a first port 415 positioned near inflatable balloon 125 and a second port 420 positioned so that it will be outside of an intubated patient's trachea and, in many instances, outside the patient's body so that ambient air may enter second port 420, pass through volume replacement channel 410, and exit through first port 415. The ambient air passing through volume replacement channel 410 and exiting through first port 415 may serve as an air supply that may improve the efficacy of suctioning air, liquid, and other matter from the patient's trachea, especially in cases where tracheal tissue or other matter forms an air-tight, or nearly air-tight, seal around tube 105 thereby cutting off a supply of air to be suctioned out via application of negative air pressure to suction line 115 and suction line port 130. Tube system 400 also includes tube 105, central lumen 110 for tube 105, suction line lumen 160, inflatable balloon 125, suction line port 130, and inflation line lumen 165, a suction line adapter 425, and an optional such as spacer 120.

In some embodiments, volume replacement channel 410 may be used as a delivery pathway for a substance (e.g., a pharmaceutical or saline) introduced into second port 420 via, for example, injection into same. The substance may be used to, for example, clean the trachea, clean the endotracheal tube, and/or provide drug delivery to the tracheal area.

We claim:

1. A tube system comprising:
   a tube that is flexible and hollow and having a first open end and a second open end, the tube comprising:
     a suction line configured to be coupled to a suction device that applies negative pressure to the suction line;
     a suction line port;
     a spacer comprising a semi-circularly shaped body that includes a first end and a second end, the first end being coupled to the tube on a first side of the suction line port and the second end being coupled to the tube on a second side of the suction line port so that an apex of the semi-circular body is not in contact with the tube; and
     an inflatable balloon affixed to, and circumferentially surrounding an exterior portion of the tube, the inflatable balloon being positioned between the first open end and the second open end of the tube.

2. The tube system of claim 1, wherein the spacer is a first spacer, the tube system further comprising:
   a second spacer positioned proximate to the suction line port.

3. The tube system of claim 1, wherein the spacer extends circumferentially around a portion of a circumference of the tube.

4. The tube system of claim 1, wherein the spacer is coupled to the tube via an extension that extends between the spacer and the exterior surface of the tube.

5. The tube system of claim 1, wherein a portion of the spacer does not touch the exterior surface of the tube.

6. The tube system of claim 5, wherein the portion of the spacer that does not touch the exterior surface of the tube is flexible and is configured to compress toward the exterior surface of the tube when a force is exerted thereon.

7. The tube system of claim 1, wherein the tube system is a tracheal tube system.

8. The tube system of claim 1, wherein an exterior surface of the spacer is smooth.

9. The tube system of claim 1, wherein spacer is affixed to the tube via at least one of a bond, a sleeve, a clip, a strap, and a clamp.

10. The tube system of claim 1, wherein the tube system is a tracheostomy tube system.

11. The tube system of claim 1, wherein the spacer is flexible.

12. The tube system of claim 1, wherein the tube further comprises:
a volume replacement channel.

13. The tube system of claim 12, wherein the volume replacement channel includes a first port positioned proximate to the inflatable balloon and a second port positioned near the second open end of the tube.

14. The tube system of claim 13, wherein a distance between the first port of the volume replacement channel is at least 10 cm away from the second port of the volume replacement channel.

15. The tube system of claim 12, wherein a distance between the first and second ports of the volume replacement channel allows for ambient air to flow into the first port and exit the second port.

* * * * *